United States Patent [19]

Hart

[11] Patent Number: 4,833,327
[45] Date of Patent: May 23, 1989

[54] HIGH-RESOLUTION RADIOISOTOPIC IMAGING SYSTEM

[76] Inventor: Hiram Hart, 3400 Wayne Ave., Bronx, N.Y. 10467

[21] Appl. No.: 43,693

[22] Filed: Apr. 29, 1987

[51] Int. Cl.$^4$ ............................................... G01T 1/164
[52] U.S. Cl. ........................... 250/363.01; 250/370.08; 250/370.09; 250/370.10
[58] Field of Search .................... 250/363 SA, 363 SB, 250/363 SC, 363 SR, 370 E, 370 G, 370 GX, 370 H, 370 I, 363 R; 378/5, 62

[56] References Cited

U.S. PATENT DOCUMENTS

| | | | |
|---|---|---|---|
| 3,965,353 | 6/1976 | Macovski | 378/5 |
| 4,473,749 | 9/1984 | Derenzo et al. | 250/363 SC |
| 4,639,599 | 1/1987 | Ichihara | 250/363 SB |
| 4,709,382 | 11/1987 | Sones | 378/62 |

OTHER PUBLICATIONS

Broude et al., "A Germanium (Lithium) Two-Crystal Compton Spectrometer", Proceedings of a Conference on Semiconductor Nuclear-Particle Detectors and Circuits, Gatlinburg, Tennessee, 1968, pp. 688–692.
Llacer et al., "Preliminary Study of a Germanium Three-Dimensional Camera for Position Emitting Radioisotopes", IEEE Transactions on Nuclear Science, vol. NS–20, 1973, pp. 282–293.
Kaufman et al., "Semiconductor Gamma-Cameras in Nuclear Medicine", IEEE Transactions on Nuclear Science, vol. NS–27, No. 3, Jun. 1980, pp. 1073–1079.
Lamarsh, Introduction to Nuclear Engineering, Addison–Wesley Publishing Company, Reading, Massachusetts, Copyright 1983, pp. 83–86.
Singh et al., "Germanium-Scintillation Camera Coincidence Detection Studies for Imaging Single Photon Emitters", IEEE Transactions on Nuclear Science, vol. NS–31, No. 1, Feb. 1984, pp. 594–598.
"Three-Dimensional Imaging of Multimillimeter Sized Cold Lesions by Focusing Collimator Coincidence Scanning (FCCS)", by H. E. Hart and S. Rudin, IEEE Transactions on Biomedical Engineering, vol. BME–24, No. 2, Mar. 1977.

Primary Examiner—Janice A. Howell
Assistant Examiner—William F. Rauchholz
Attorney, Agent, or Firm—Kirschstein, Kirschstein, Ottinger & Israel

[57] ABSTRACT

A high-resolution radioisotopic imaging system employs spaced-apart non-contiguous thin and thick electronic collimation detectors arranged about a radioisotopic source field of radioisotopic atoms, each operative for detecting a plurality of gamma rays, or at least one position, or a combination of at least one position and at least one gamma ray. The detectors specify a plurality of emission probability fields which intersect in space to form a reduced emission probability field.

4 Claims, 2 Drawing Sheets

HIGH-RESOLUTION RADIOISOTOPIC IMAGING SYSTEM

BACKGROUND OF THE INVENTION

1. Field of the Invention

This invention generally relates to the determination of the three-dimensional distribution and intensity of multiple radioisotopic sources of essentially unknown spatial and/or temporal characteristics in the presence of noise by means of appropriate measurement and analysis and, more particularly, to a radioisotopic imaging system for accurately reconstructing with a high spatial resolution three-dimensional distributions of radioactivity of the kind encountered in lesion detection in nuclear medicine.

2. Description of Related Art

Radioisotopic organ imaging is customarily carried out by (a) administering a gamma ray emitting isotope to a patient, (b) determining the radioisotopic distribution and intensity in the organ by detecting gamma rays exiting the organ, and (c) analyzing the detected gamma ray data. The detection is performed by collimator detector assemblies which have fields of view which must be taken into account.

Focussing collimators were employed initially for selectively detecting radiation emitted within an approximately cylindrical field of view extending through the focal region as specified by their point source response function (PSRF). The clinical imaging procedure consisted of moving a collimator detector assembly along a series of planar parallel lines relative to the patient and generating a raster output.

Focussing collimator systems were not well adapted to study dynamic phenomena such as cardiac function and have generally been replaced by gamma cameras which continuously detect gamma rays emitted from the whole region of interest. This was done with parallel hole or pin-hole collimators, each of which served to define a restricted field of view necessary for effective determination of the radioisotopic tissue distribution.

For three-dimensional imaging, it was necessary to view the tissue of interest at many different angles and to analyze the data with the aid of a computer using one or more standard image processing algorithms. Collimation limited the gamma rays arriving at the detectors and less than about one-thousandth of all gamma rays exiting the patient were detected. The number of detections or counts recorded in individual pixels (data elements) was variously limited by this inefficiency, by the energy resolve time of the sodium iodide (NaI) crystal detectors generally used (about 250 ns), by the practical time limit for patient immobilization (about 10–15 minutes), and by patient and personnel radiation exposure safety considerations. Statistical fluctuations were therefore quite significant.

The field of view defined by each channel in the parallel-hole collimator was a solid diverging cone specified by the channel geometry. A true pin-hole collimator had zero detection efficiency. However, in practice, the pin holes had significantly non-zero dimensions. Together with the uncertainty in specifying the exact site of the gamma ray-crystal detector interaction, the emission probability field (EPF) associated with a single gamma ray-induced crystal flash using pin-hole collimation was again a solid diverging cone.

Because of the relatively large proportion of statistical noise and the imprecision associated with the solid diverging conical emission probability fields (EPFs) defined by individual measured events, the tomographic cold lesion detection limit attainable in standard clinical nuclear imaging was about one to two cubic centimeters using a single photon emission computed tomography (SPECT) system. This limit was well above that attainable with other higher resolution imaging modalities.

Nonetheless, radioisotopic organ imaging continued to be very important as an index of physiological function as distinguished from other types of anatomical properties. In an effort to improve the resolution possible in radioisotopic imaging, positron-emission tomography (PET) was developed. A variety of different systems existed, but they were all based upon coincidence-counting the 0.511 Mev gamma ray pairs arising from positron-electron annihilation and specifying the almost straight angle (about 180°) between the gamma rays of each pair. Since the generally cylindrical EPF extending about and along the path of propagation in a PET system was generally smaller than the solid diverging conical zone of earlier methods, somewhat higher resolutions were achieved. The limit on resolution in a PET system arose, among other factors, from the mean free path of the positron prior to capture in a detector, the deviation from a straight angle path of each pair of gamma rays due to the residual momentum of the positron prior to annihilation, the longitudinal uncertainty in the annihilation site, and the interaction site uncertainty in the about three cubic centimeter thick unshielded NaI detectors usually used. These relatively large, thick detectors were required to absorb the high energy gamma rays and to exclude secondary gamma rays arising from Compton scattering within the tissue of interest. Denser, more compact, solid-state, thinner detectors were also used to reduce this latter limitation. Time of flight information was used to try to reduce the emission probability field along the longitudinal direction, but even a 0.2 nanosecond resolve time involves an annihilation site longitudinal ambiguity of about six centimeters.

Mechanical detector wobbling has also been proposed as a means of improving the resolution. In general, however, cold lesions less than about one to two cubic centimeters remained undetected. In view of the specialized facilities required for the short-lived isotopes commonly used (medical cyclotrons) and the limited improvement in resolution, PET systems have not found general application.

A focussing collimator coincidence scanning (FCC) system with very small lesion detection capability (resolutions less than about 0.01 cm$^3$) was proposed by H. Hart and S. Rudin, IEEE Trans. Biomed. Eng., BME-24,169,1977, and was based upon coincidence detection of gamma rays from isotopes which emitted more than one gamma ray in cascade. By using multiple focussing collimators with intersecting fields of view, coincidence events served to define a very small focal region. Laboratory detection of structures having a volume of less than 0.01 cm$^3$ was reported.

The sensitivity of the FCC system was, however, very low. Clinical scan times would have been generally unacceptable on a routine basis. Dynamic imaging was not possible. The FCC approach has not been clinically applicable.

A system including a single pair of uncollimated planar detectors was proposed by M. Singh and D. Dario in IEEE Trans., Nuc. Sci., NS-31,594; 1984. Electronic collimation was substituted for material absorption collimation. This substitution greatly improved the sensitivity possible for gamma cameras. The resolution reported with a prototype system seemed to be considerably greater than one centimeter. The ultimate resolution possible appeared to be limited since the emission field defined by a two-fold (thin-thick detector) coincidence event is a relatively large hollow conical shell whose wall thickness is a function of the uncertainties in the detector interaction sites and the Compton scattering deflection angle arising from the finite energy resolution of the thin detector component of the system. See, also, L. Kaufman et al., IEEE Trans., Nuc. Sci., NS-27, 1073, 1980.

In all previously known radioisotopic systems, there has been no radioisotopic imaging system demonstrated or proposed capable of practical, clinical, dynamic, tomographic imaging on a clearly sub-cubic centimeter scale. Such a capability would be extremely important, both clinically and in research.

SUMMARY OF THE INVENTION

1. Objects of the Invention

It is an object of this invention to overcome the drawbacks of prior art radioisotopic imaging systems.

It is another object of this invention to provide a high-resolution, radioisotopic imaging system which is practical, both for research and especially for clinical use, and which can image a radioactive distribution on a sub-cubic centimeter scale.

2. Features of the Invention

In keeping with these objects, and others which will become apparent hereinafter, one feature of this invention resides, briefly stated, in a high-resolution radioisotopic imaging system which comprises detector means including a plurality of electronic collimator detector elements arranged about a radioisotopic source field of radioisotopic atoms, each operative for substantially simultaneously emitting a plurality of photons, e.g. gamma rays. The detector means detects the gamma rays emitted substantially simultaneously from a radioisotopic atom. The detector means specifies a plurality of emission probability fields which intersect in space to form a reduced emission probability field. Hence, high-resolution imaging of the source field is obtained. In a variant embodiment, at least one nuclear gamma ray and a positron are substantially simultaneously emitted from a radioisotopic atom. The positron is annihilated into two gamma rays. In another variant, each radioisotopic atom emits only a positron which is annihilated as before.

DETAILED DESCRIPTION OF THE PREFERRED EMBODIMENTS (A) Double Nuclear Gamma Coincidence Mode:

The above cited drawbacks of the prior art can now be substantially overcome by a coincident measuring and data processing system which tends, for each coincident event, to optimally specify the site of simultaneous emission of a plurality of gamma rays.

The new approach sharply reduces the overall emission probability field for the site of an isotope decaying with multiple gamma emissions by using electronic collimation and by intersecting the individual coincident gamma ray emission probability fields. System resolution is dramatically increased while retaining adequate sensitivity.

Figure 1:
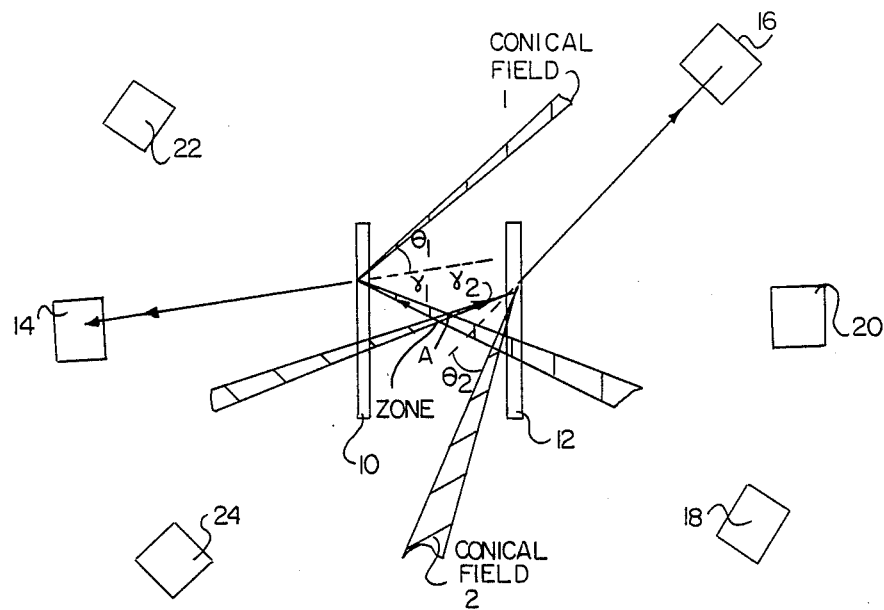
FIG. 1 is a schematic diagram depicting the operation of the gamma-ray detection components of a tomographic imaging system comprising a plurality of thin crystal detectors near a radioisotopic source field and a plurality of more distant thick crystal detectors, the source field being an isotope which emits two nuclear gamma rays $\gamma_1$ and $\gamma_2$ at the same time (in cascade)

Referring now to FIG. 1, a plurality of thin, solid-state, high-purity germanium (HpGe) detectors 10, 12 are arranged about a field source represented by point A. Although only two planar detectors are shown, this invention is not intended to be so limited since more than two detectors can also be arranged around source A. In another variant, a single or multiple, thin, curved detectors can be employed in order to circumferentially surround source A.

The source A is an isotope which emits radiation. As the description proceeds, the radiation can be one or more nuclear gamma rays or positron annihilation gamma rays, or a combination of nuclear and annihilation gamma rays. The isotope is administered to a patient in medical diagnosis and is distributed throughout a tissue to be examined.

The thin detectors 10, 12 are crisscrossed with a non-illustrated first set of vertically-extending parallel slots on one major surface. On the other major surface is a second set of horizontally-extending parallel slots. The interaction of a gamma ray at or in the vicinity of one or more crossings of the slots is electrically detected in known manner. The thin detector, i.e. a hodoscope, is entirely conventional in this art and requires no further elaboration. See Kaufman et al., supra. The thinness of the detector serves to insure that, in general, only one scattering event of the impinging gamma ray occurs therein. Not only can the thin detector detect the location of the impingement of the gamma ray, but by measuring the energy released, the deflection angle $\theta$ (see $\theta_1$ and $\theta_2$ for representative rays $\gamma_1$ and $\gamma_2$) from the Compton scattering equation can also be determined.

Also entirely conventional in this art are thick, solid-state, detectors 14–24 arranged about the field source A radially outwardly beyond the thin detectors. The thickness of the detectors 14–24 in which multiple scattering of gamma rays occurs, insures that the gamma rays will almost always be stopped therein. The thick detectors serve to fix the location of the stopped gamma rays. Although only six thick detectors are shown, more or fewer than six detectors could be employed. Indeed, a single continuous spherical array is within the spirit of this invention.

In FIG. 1, source A is of the type which emits two gamma rays $\gamma_1$ and $\gamma_2$ which impinge on thin detectors 10, 12 at known locations, and which pass through the thin detectors to eventually impact on the thick detectors 14, 16. Deflection angles $\theta_1$ and $\theta_2$ are measured relative to the continuation of the trajectory of a respective gamma ray to its thick detector. The simultaneous detection of impingements on detectors 10 and 14 defines a first emission probability field 1 which subtends a hollow, conical space whose apex is situated at the respective thin detector 10. The simultaneous detection of impingements on detectors 12 and 16 defines a second emission probability field 2 which subtends another hollow, conical space whose apex is situated at the respective thin detector 12. The simultaneous detection of impingements on detectors 10, 12, 14 and 16, therefore, defines a reduced emission probability field or zone in space which is the intersection of fields 1 and 2.

The deflection angle $\theta_1$ occurring at the thin detector 10 is approximately specified by the measured energy of the interaction occurring in the thin detector 10 in accordance with the conventional Compton scattering formula. The sum of the two measured energies at detectors 10 and 14 approximates that of an unscattered primary gamma ray in order for the coincidence event to be considered. The sites of interaction and the angle of deflection $\theta_1$ specify the hollow conical gamma ray emission probability field 1 whose apex is also an area representing the positional uncertainty of the thin detector interaction and whose thickness is a function of the angle of deflection uncertainty associated with tee energy resolution of the thin detector and the positional uncertainty of the thick detector site of interaction.

The same analysis pertains to the interaction of $\gamma_2$ with detectors 12 and 16. The deflection angle $\theta_2$ can again be estimated with the conventional Compton scattering formula, and the hollow conical emission field 2 specified.

Since modern solid-state thin detectors such as HpGe are capable of less than about one nanosecond resolve times, the overall four detector coincidence most probably arises from a single nuclear decay of an isotope emitting a plurality of gamma rays in cascade. The site of this decay logically then lies within the aforementioned very much restricted zone specified by the intersection of conical fields 1 and 2. Considerable improvement in resolution is therefore possible.

It is noted that for both $\gamma_1$ and $\gamma_2$ the positions of the apices of the emission probability fields 1 and 2 are rather precisely determined by the interaction sites at the thin detectors with the cone half angle specified by the thin detector interaction energy. The thick detectors provide the information necessary for cone orientation while the pairs of summed energies (thin and thick) distinguish between incident primary and tissue scattered gamma rays.

(B) Positron Emission Coincidence Mode

Figure 2:
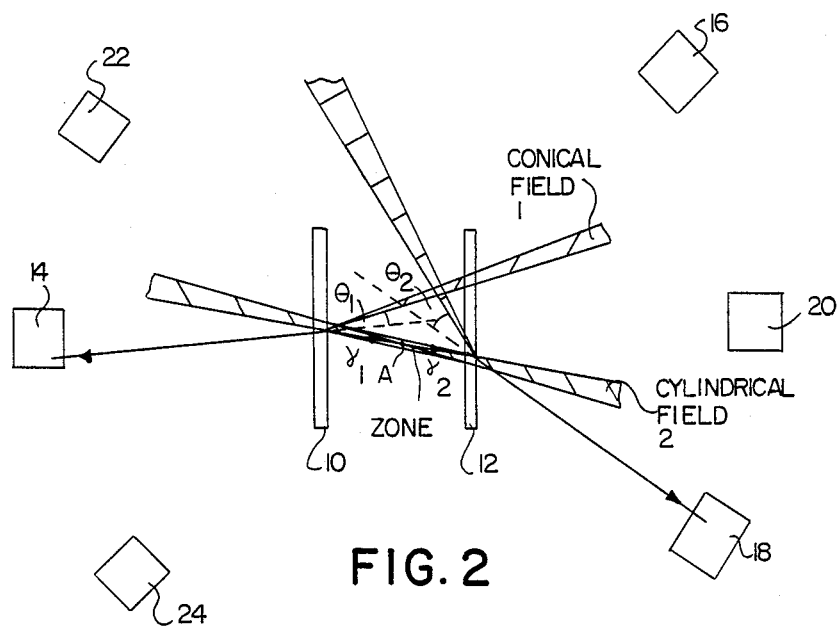
FIG. 2 is a schematic diagram depicting the operation of the system of FIG. 1, but for a source field isotope emitting a positron that forms annihilation gamma rays $\gamma_1$ and $\gamma_2$.

The prior constraint of intersecting conical fields applicable to double nuclear gamma rays directly pertains also in reduced form to annihilation rays $\gamma_1$ and $\gamma_2$ of FIG. 2. Since annihilation rays $\gamma_1$ and $\gamma_2$ are about 180° apart, the path of propagation is now contained in the approximately cylindrical emission probability field common to both conical fields. For a four-detector coincidence (two pairs of thin-thick detector interactions), there is no advantage over the thin-thick contiguous detector arrangement proposed by Llacer and Cho in IEEE Trans., Nuc. Sci.-20, 282, 1973.

For more probable three-fold coincidence events (one thin-thick detection, one thick detection), however, the substantially increased separation between the thin and thick detectors now considerably decreases the effect of the position uncertainty in the thick detector interaction. For two-fold coincidence events (one thick detector, one thick detector), the geometry reduces to a standard positron emission tomography system.

(C) Positron Emission-Nuclear Gamma (PENG) Coincidence Mode

Consider system operation with a field source at point A emitting both a positron and at least one nuclear gamma ray simultaneously. For simplicity, assume the most probable, high resolution, accessible event, i.e. a four-fold coincidence in which both annihilation gamma rays $\gamma_1$ and $\gamma_2$ interact only with the thick detectors, thereby defining a generally cylindrical emission probability field, and a thin-thick detector interaction for the nuclear gamma ray $\gamma_3$, thereby defining a hollow cone emission probability field, as described above.

Figure 3:
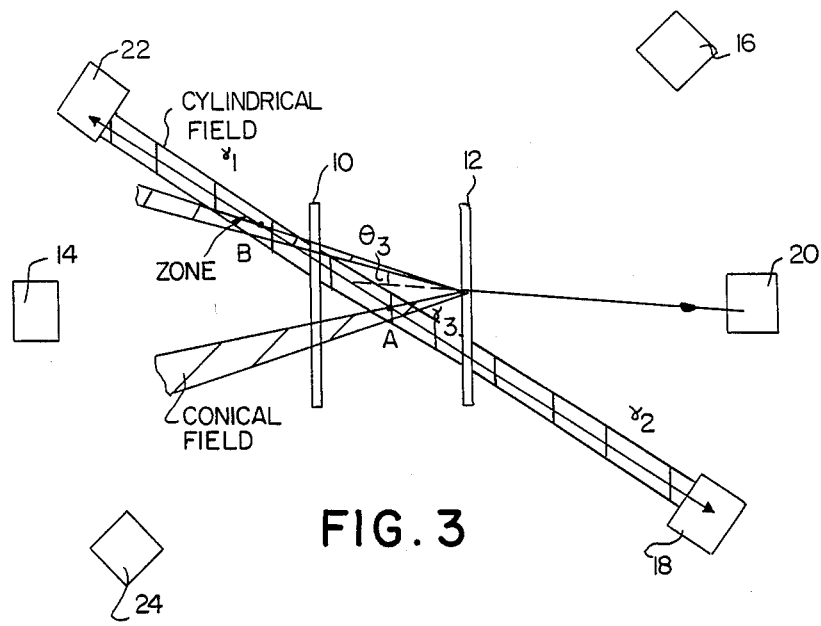
FIG. 3 is a schematic diagram depicting the operation of the system of FIG. 1, but for a source field isotope emitting a positron that forms annihilation gamma rays $\gamma_1$ and $\gamma_2$ and, at the same time, a nuclear gamma ray $\gamma_3$.

As seen in FIG. 3, the overall emission probability field is now reduced to the intersection of the cylindrical field and the conical field resulting in general in, at most, two approximately cylindrical zones. The thickness of these zones is generally smaller by an order of magnitude than is currently obtainable with time-of-flight positron emission tomography. Note that with the far less probable three- or four-fold coincident interactions of the annihilation gamma rays (five- or six-fold coincidences in all), the emission probability field cylinder diameter is further reduced, resulting in a still smaller emission probability field.

Although the reduced emission probability field, as described above, is clearly much smaller than in prior art systems, and therefore much more suitable for high resolution, the multi-fold coincidence requirement also reduces the effective sensitivity of the system. It is necessary therefore, to estimate the sensitivity of the system in different modes of operation.

(D) Sensitivity

1. General Considerations

The multi-fold coincidence requirement necessary for an emission probability field reduced in size by intersecting fields reduces the overall sensitivity of system operation. At least six factors serve to limit the probability of a single gamma ray being usefully detected, viz:
 (a) tissue scatter and absorption;
 (b) system solid angle (thin detectors);
 (c) thin detector penetration;
 (d) thin detector double scattering;
 (e) thin-thick detector geometric compatibility;
 (f) thick detector penetration (in full or partially).

The separate factors and related design considerations will be estimated in order:

(a) Tissue scatter and absorption:

Assuming a gamma ray energy of ~0.500 Mev and a model for a human head of a six inch diameter sphere of water then the average probability that no tissue scatter and absorption in water will occur is:

$$e^{-\mu_0(3'')} = e^{-(0.10)(7.5)} = e^{-0.75} = 0.472$$

Assuming a ten inch diameter cylinder as a suitable model for the human torso, then:

$$e^{-\mu\sigma(5'')} = e^{-1.25} = 0.29$$

Since the total for tissue absorption and scatter rises steeply for gamma ray energies less than ~70 kev, multiple coincidences become less probable for gamma ray energies of less than 70 kev.

(b) System solid angle (thin detectors):

For a ring system of multiple thin detector hodoscopes arranged about the head a solid angle of approximately 35% (of $4\pi$) is close to maximum considering gaps, etc. between detectors. For a ring and cap system, a solid angle o approximately 50% may be attainable.

For a ring (cylinder) of thin detectors about the torso, the solid angle is not likely to exceed 30%.

(c) Thin detector penetration:

In order to limit the probability of double Compton scattering within the thin detector, only a 20% probability of a Compton interaction is assumed. For a ~500 kev gamma ray at close to normal incidence, this implies a thickness ~0.4 cm.

Figure 4:
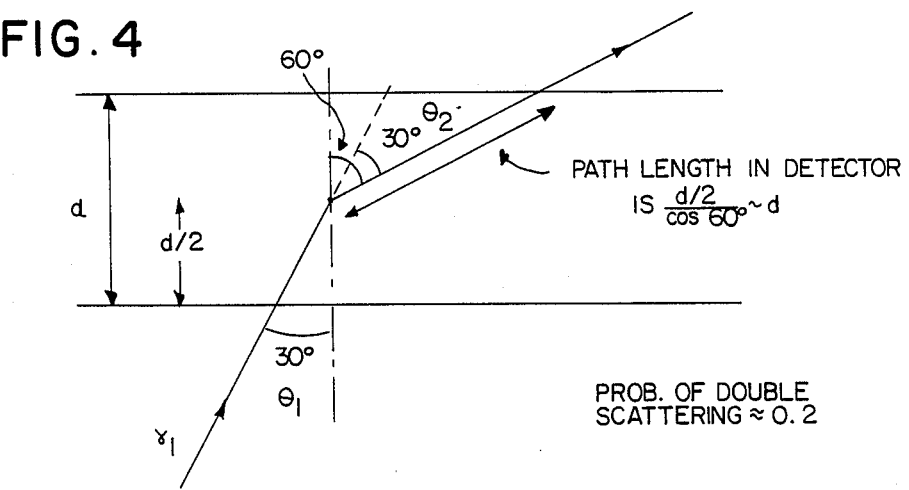
FIG. 4 is a diagram depicting the geometry associated with possible double scattering in a thin detector for the FIG. 1 system.

(d) Thin detector double scattering:

Referring to FIG. 4, the incident gamma ray $\gamma_1$ enters at an assumed angle $\theta_1$ of 30° with respect to the normal. Halfway into the detector, the ray $\gamma_1$ experiences a deflection angle $\theta_2$ of 30°. The subsequent path length is defined as d, and results in an approximate likelihood of avoiding double scattering of 0.8. This probability of 0.8 for avoiding double scattering within the thin detector, though obviously approximate, is likely to be realistic. Note that if the 20% probability of a single Compton interaction is raised by increasing the thin detector thickness, the likelihood of unwanted double scattering also rises in partial compensation (i.e. $0.20 \times 0.80 = 0.16$; $0.30 \times 0.70 = 0.21$). Note also that since the above probabilities are functions of the incident gamma ray energies, the optimal thin detector thickness for a range of gamma ray energies, i.e. multiple nuclear gamma rays, must represent a compromise.

(e) Thin-thick detector geometric compatibility

Figure 5:
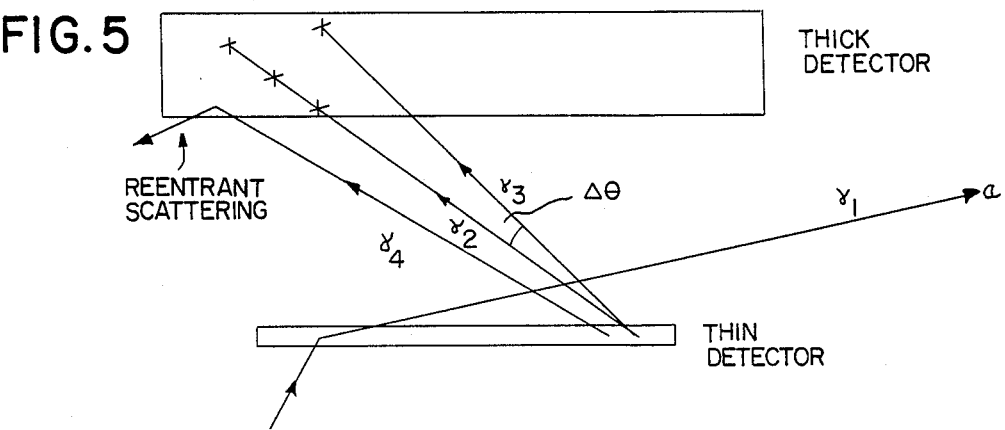
FIG. 5 is a diagram depicting the geometric parameters of importance in estimating the efficiency and accuracy of detection in thin-thick electronic collimation systems.

Referring to FIG. 5, it is clear that the gamma ray $\gamma_1$ exiting at a is a lost event. Somewhat less obvious is the imprecision and loss of sensitivity associated with the thin-thick planar pairs of detectors used in prior electronic collimation techniques. Referring to gamma rays $\gamma_2$ and $\gamma_3$, it is clear that for such obliquely incident gamma rays the ambiguity in the depth at which the thick detector interaction occurs results in a significant positional ambiguity. This, in turn, results in a loss in precision in the orientation of the emission probability field cone (i.e. $\Delta\theta$). This ambiguity $\Delta\theta$ can, of course, in principle be reduced by increasing the thin-thick detector spacing or even invoking multiple layers of "thick" detectors, but the latter solution has practical limitations.

Finally, referring to gamma ray $\gamma_4$, also obliquely incident, it is apparent that a significant loss in such events will occur because of re-entrant Compton scattering. For the above reasons, the thick detector in the standard planar pair has now been replaced by a whole continuous spherical surface array of thick detectors sufficiently distant from the thin detectors and the region being imaged to insure close to normal incident gamma rays, and to insure that the uncertainty in the interaction site in the thick detector does not seriously compromise emission probability field cone orientation. Since Compton scattering occurs over a 360° solid angle, it will be assumed that even for the assumed improved geometry, the probability of thin-thick detector coincidence is 0.5.

(f) Thick detector penetration

Since resolve times increase with detector thickness, compromise is necessary. The likelihood of complete gamma ray absorption in the thick detector is taken to be 0.9.

2. Multi-nuclear gamma ray mode

Combining the above factors (a) through (f), the likelihood of effective two-fold thin-thick detector coincidence measurement of a single nuclear gamma ray is:

Head:
$$\frac{P(NG)}{1\text{Brain}} = 0.472 \times 0.500 \times 0.20 \times 0.80 \times 0.50 \times 0.9 = 0.017$$

Torso:
$$\frac{P(NG)}{1\text{Torso}} = 0.29 \times 0.30 \times 0.20 \times 0.80 \times 0.50 \times 0.9 = 0.0063$$

The probability of detecting a two gamma ray four-fold (thin-thick detector; thin-thick detector) coincidence in brain imaging is therefore $= 2.89 \times 10^{-4}$. This probability is of the same order of magnitude as that with current single gamma ray systems whose emission probability fields are, of course, much larger than defined by intersecting conical fields.

The probability of detecting a two gamma ray, four-fold coincidence in torso imaging is $\sim 3 \times 10^{-5}$. For an isotope emitting n nuclear gamma rays the sensitivity is increased by the factor $C_2^n$.

Although the emission probability field defined by three intersecting conical EPFs would be relatively small, the probability of detecting a three nuclear gamma ray, six-fold coincidence (brain imaging) is probably too low to be useful $= (0.17)^3 \approx 5 \times 10^{-6}$. If an isotope emits n nuclear gamma rays, the sensitivity would be increased by the factor $C_3^n$.

3. PET Mode

For a four-fold coincidence, the probability of the first annihilation gamma ray being detected by thin and thick detectors inring-cap brain imaging is:

$$\approx 0.472 \times 0.50 \times 0.20 \times 0.80 \times 0.50 \times 0.9 = 0.017$$

Assuming for a ring-cap brain imaging geometry that if the first gamma ray is incident upon detectors, the probability for a second annihilation gamma ray detection is increased by the straight angle correlation $$\approx 0.472 \times 0.80 \text{ (correlation factor)} \times 0.20 \times 0.80 \times 0.50 \times 0.9 \approx 27.0 \times 10^{-3}$$

The probability for a four-fold coincidence with PET in brain imaging is:

$$\frac{P(PET)}{4B} \approx 0.017 \times 0.027 \approx 4.6 \times 10^{-4}$$

The probability for a three-fold coincidence (one thin-thick detector, one thick detector) is:

For annih. ray $\gamma_1$; $P_1 \approx 0.017$ (thin-thick detector)

For annih. ray $\gamma_2$; $P_2 \approx 0.472 \times 0.80 \times 1.00 \times 0.50 \times 0.9 \approx 0.17$ $$P(PET)_{3B} = P_1 \times P_2 + P_2 \times P_1 = 2[0.017][0.17]$$

$$P(PET)_{3B} = 2[.00289] = .0058 \approx 0.58\%$$

The probability for a two-fold coincidence is:

$$P_{.1B} = 0.472 \times 0.50 \times 0.80 \times 1.00 \times 1.0 \times 0.9 = 0.17$$

$$P_{2B} = 0.472 \times 0.80 \times 0.80 \times 1.00 \times 1.0 \times 0.9 = 0.27$$

$$P(PET)_{2B} = 0.17 \times 0.27 \approx 0.046 = 4.6\%$$

4. Positron emission-nuclear gamma ray mode (PENG)

The probability of a two-fold PET (thick-thick detector) coincidence an a two-fold, thin-thick detector, nuclear gamma ray coincidence is for brain scanning:

$$P(PENG)_{4B} = P(PET)_{2B} \times P(NG)_{2B} = 0.046 \times 0.017$$

$$P(PENG)_{4B} \approx 8 \times 10^{-4}$$

This probability is at least as high as in standard single photon emission computed tomography (SPECT) and is associated with a reduced emission probability field (intersection of a hollow cone and cylinder) which is very much smaller than SPECT. Note also that if n nuclear gamma rays are simultaneously emitted by a positron emitter, then the sensitivity is further increased by the factor n.

5. Emission Probability Field (EPF) Specification:

Single gamma ray thin-thick detector interaction conical EPF

Let $(X_1,Y_1,Z_1)$ and $(X_2,Y_2,Z_2)$ be the coordinates of the thin and thick detector interaction sites. The scattering angle $\theta$ is determined from the Compton scattering equation and the measured energy at the thin detector. The equation of the axis of the cone is:

$$\frac{X - X_1}{X_2 - X_1} = \frac{Y - Y_1}{Y_2 - Y_1} = \frac{Z - Z_1}{Z_2 - Z_1} \text{ or}$$

$$\frac{X - X_1}{a} = \frac{Y - Y_1}{b} = \frac{Z - Z_1}{c}$$

where $a = X_2 - X_1$, $b = Y_2 - Y_1$, $c = Z_2 - Z_1$, are the direction numbers.

The line between a field point voxel (x,y,z) and the thin detector interaction site $(X_1,Y_1,Z_1)$ is given by the equation:

$$\frac{X - X_1}{x - X_1} = \frac{Y - Y_1}{y - Y_1} = \frac{Z - Z_1}{z - Z_1} \text{ or}$$

$$\frac{X - X_1}{a'} = \frac{Y - Y_1}{b'} = \frac{Z - Z_1}{c'}$$

where $a' = x - X_1$, $b' = y - Y_1$, $c' = z - Z_1$, are the direction numbers.

Voxels at or near the conical surface of the EPF therefore satisfy the condition:

$$\cos(\theta + \Delta\theta) \leq \frac{aa' + bb' + cc'}{\sqrt{a^2 + b^2 + c^2} \sqrt{a'^2 + b'^2 + c'^2}} \leq \cos(\theta - \Delta\theta)$$

where $\pm\Delta\theta$ is the angular uncertainty arising from the finite energy resolution of the thin detector and the interaction site uncertainty in the thick detector.

Voxels within the intersection of two cones would, of course, satisfy the conditions:

$$\cos(\theta_1 + \Delta\theta_1) \leq \quad \text{Equation I}$$

$$\frac{a_1a_1' + b_1b_1' + c_1c_1'}{\sqrt{a_1^2 + b_1^2 + c_1^2} \sqrt{a_1'^2 + b_1'^2 + c_1'^2}} \leq \cos(\theta_1 - \Delta\theta_1)$$

for the first cone as above and also $$\cos(\theta_2 + \Delta\theta_2) \leq \quad \text{Equation II}$$

$$\frac{a_2a_2' + b_2b_2' + c_2c_2'}{\sqrt{a_2^2 + b_2^2 + c_2^2} \sqrt{a_2'^2 + b_2'^2 + c_2'^2}} \leq \cos(\theta_2 - \Delta\theta_2)$$

where $a_2 = X_4 - X_3$, $b_2 = Y_4 - Y_3$, $c_2 = Z_4 - Z_3$ and $a_2' = x - X_3$, $b_2' = y - Y_3$, $c_2' = z - Z_3$ with $(X_3,Y_3,Z_3)$ and $(X_4,Y_4,Z_4)$ the coordinates of the thin-thick detector interaction sites for the second nuclear gamma ray.

Weighting factors can be assigned to voxels satisfying equations I and II, depending upon how close they are to the intersecting conical surfaces (i.e. for $\Delta\theta_1$ and $\Delta\theta_2 \approx 0$).

The analysis for a cylindrical EPF associated with PET follows similarly. The equation of the axis of he cylindrical field is:

$$\frac{X - X_1}{X_2 - X_1} = \frac{Y - Y_1}{Y_2 - Y_1} = \frac{Z - Z_1}{Z_2 - Z_1} \text{ or}$$

$$\frac{X - X_1}{a} = \frac{Y - Y_1}{b} = \frac{Z - Z_1}{c}$$

where $(X_1,Y_1,Z_1)$ and $(X_2,Y_2,Z_2)$ are the coordinates of the two annihilation gamma rays initial detector interaction sites. Those voxels lying within a distance $\delta$ from the axis are included in the cylindrical EPF, where $\delta$ is a measure of the uncertainties associated with PET. For a voxel with coordinates (x,y,z), the perpendicular distance from the cylinder axis is given by:

$$PD = \left[ (a'^2 + b'^2 + c'^2) - \frac{(aa' + bb' + cc')^2}{a^2 + b^2 + c^2} \right]^{\frac{1}{2}} \text{ where}$$

$$\begin{cases} a' = X_1 - x, \ b' = Y_1 - y, \ c' = Z_1 - z \\ a = X_1 - X_2, \ b = Y_1 - Y_2, \ c = Z_1 - Z_2 \end{cases}$$

Voxels within the intersection of the cone and the cylinder in PENG imaging satisfy the following equations:

$$PD = \qquad \text{Equation III}$$

$$\left[ (a'^2 + b'^2 + c'^2) - \frac{(aa' + bb' + cc')^2}{a^2 + b^2 + c^2} \right]^{\frac{1}{2}} \leq \delta$$

and $$\cos(\theta_1 + \Delta\theta_1) \leq \qquad \text{Equation IV}$$

$$\frac{a_1 a_1' + b_1 b_1' + c_1 c_1'}{\sqrt{a_1^2 + b_1^2 + c_1^2} \sqrt{a_1'^2 + b_1'^2 + c_1'^2}} \leq \cos(\theta_1 - \Delta\theta_1)$$

Weighting factors can be assigned to voxels satisfying Equations III and IV, depending upon how small PD is and how close the quotient in Equation IV is to $\cos(\theta_1)$.

(E) Detectors and Associated Electronics

The circuitry required for electronic collimation with a single pair of thin-thick detectors described by Singh in the above identified reference is readily modified to accommodate the much larger number of detectors in this system. Note that while the thin detectors remain HpGe hodoscopes as described by Singh, the thick detectors are now solid-state as well, i.e. probably also HpGe to provide for shorter resolve times and that coincidences are now allowed between any geometrically appropriate pair of thin-thick detectors. The logic is somewhat more complex, therefore, but noise from extraneous gamma rays may be less of a problem in that since there are many thin and thick detectors, acceptable events will only be compromised if an extraneous gamma ray interacts with one of the two thin-thick detectors instantaneously recording a true event.

The thick detectors should be large enough to effectively absorb most of the primary gamma rays anticipated and sufficiently distant from the thin detector hodoscopes that positional uncertainties in the thick detector interaction sites do not introduce an error in the EPF cone orientation of more than ~2°. The thick detectors may themselves be hodoscopes to further reduce positional uncertainty, but this may not be necessary.

Note also that the enlarged assembly and spacing between the thin and thick detectors increases the overall size of the system and the associated cryogenic requirements.

(F) Image Processing

Standard radioisotopic image processing generally assumes a uniform point source response function (PSRF) arising from fixed geometric and/or electronic characteristics. It is obvious that the intersecting EPFs described above can vary grossly from event to event. Nonetheless, a point source imaged by the system as proposed will exhibit a characteristic unprocessed image and this can define an operational system PSRF. Because the thin detector hodoscopes are employed in relatively close proximity to the region of interest, however, the PSRF may vary in amplitude and shape from point to point, depending upon whether, for example, the source element is centrally located or near a surface. It follows, then, that the uniformity of the PSRF has to be examined carefully and, if it is not uniform, compensated for in carrying out image processing.

(G) Radioisotopes

By way of non-limiting examples, any one of the following radioisotopes can be employed for substantially simultaneously emitting multiple nuclear gamma rays:

$Ir^{192}$, $K^{43}$, $I^{130}$, $Br^{82}$, $Tl^{194}$, $Ir^{194m2}$, $Au^{200m}$, $Tl^{196}$, $Tl^{198}$, $Hf^{178}$, $Hf^{179}$, $Hf^{180}$, $Ta^{186}$, $Ir^{190}$, $Ta^{178}$, $Pm^{144}$, $Au^{190}$, $Rh^{101}$, $V^{48}$, $Tc^{94}$, and $Hg^{197}$.

Any one of the following radioisotopes can be employed as positron emitters and for emitting nuclear gamma ray or rays: $K^{38}$, $Sc^{43}$, $Sc^{48}$, $Cr^{49}$, $As^{74}$, $Br^{77}$ and $Tc^{94}$.

It will be understood that each of the elements described above, or two or more together, also may find a useful application in other types of constructions differing from the types described above.

While the invention has been illustrated and described as embodied in a high-resolution radioisotopic imaging system, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

I claim:

1. A high-resolution radioisotopic imaging system for imaging a source field with sub-cubic centimeter resolution, comprising:

inner electronic collimator detector means spaced radially outwardly from a radioisotopic source field of radio-isotopic atoms, each atom radioactively decaying to substantially simultaneously emit a plurality of gamma rays, said inner detector means being operative for detecting and scattering gamma rays impinging thereon;

outer electronic collimator detector means spaced radially outwardly from the inner detector means, and operative for detecting and substantially fully absorbing the gamma rays scattered form the inner detector means;

said inner and outer detector means being operative, when a first gamma ray is simultaneously detected by the inner and outer detector means, for specifying a first emission probability field in space;

said inner and outer detector means being operative, when a second gamma ray is simultaneously detected by the inner and outer detector means, for specifying a second emission probability field in space; and said inner and outer detector means being so arranged relative to one another that the first and second emission probability fields intersect each other in space and form a reduced zone in space for imaging the source field with sub cubic centimeter resolution.

2. The imaging system of claim 1, wherein each radioisotopic atom emits a positron which annihilates into the gamma rays.

3. The imaging system of claim 1, wherein each radioisotopic atom emits a gamma ray and a positron.

4. The imaging system of claim 1 and further comprising means for generating form a point source a point source unprocessed image as a function of said emission probability fields, for generating from the source field a source field unprocessed image as a function of said emission probability fields, and for generating a processed image as a function of said point source unprocessed image and said source field unprocessed image.

* * * * *